United States Patent
Yagi et al.

(10) Patent No.: US 7,017,575 B2
(45) Date of Patent: *Mar. 28, 2006

(54) OXYGEN SUPPLY APPARATUS, CONTROLLER FOR THE OXYGEN SUPPLY APPARATUS, AND RECORDING MEDIUM FOR THE CONTROLLER

(75) Inventors: Hideaki Yagi, Aichi (JP); Junichi Akiyama, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/957,030

(22) Filed: Sep. 21, 2001

(65) Prior Publication Data

US 2002/0038657 A1 Apr. 4, 2002

(30) Foreign Application Priority Data

Sep. 21, 2000 (JP) .............................. 2000-287110

(51) Int. Cl.
*A62B 7/00* (2006.01)

(52) U.S. Cl. .............................. 128/205.11; 128/204.18

(58) Field of Classification Search ........... 128/205.11, 128/204.26, 204.21, 204.23, 204.18
See application file for complete search history.

(56) References Cited

U.S. PATENT DOCUMENTS

| | | | | | |
|---|---|---|---|---|---|
| 3,794,026 | A | * | 2/1974 | Jacobs .................... | 128/200.13 |
| 4,256,101 | A | * | 3/1981 | Ellestad ................. | 128/204.23 |
| 4,340,044 | A | * | 7/1982 | Levy et al. ............. | 128/204.21 |
| 4,357,936 | A | * | 11/1982 | Ellestad et al. ........ | 128/204.23 |
| 4,681,099 | A | * | 7/1987 | Sato et al. ............. | 128/204.23 |
| 4,686,974 | A | * | 8/1987 | Sato et al. ............. | 128/204.23 |
| 4,706,664 | A | * | 11/1987 | Snook et al. .......... | 128/204.23 |
| 4,823,788 | A | * | 4/1989 | Smith et al. ........... | 128/205.24 |
| 5,137,017 | A | * | 8/1992 | Salter ..................... | 128/207.18 |
| 5,148,802 | A | | 9/1992 | Sanders et al. | |
| 5,316,009 | A | * | 5/1994 | Yamada ...................... | 600/533 |
| 5,385,142 | A | * | 1/1995 | Brady et al. ........... | 128/204.23 |
| 5,503,146 | A | * | 4/1996 | Froehlich et al. ...... | 128/204.23 |
| 5,590,648 | A | * | 1/1997 | Mitchell et al. ............ | 600/301 |

(Continued)

FOREIGN PATENT DOCUMENTS

JP 8-187289 7/1996

*Primary Examiner*—Henry Bennett
*Assistant Examiner*—Dinnatia Doster Green
(74) *Attorney, Agent, or Firm*—Sughrue Mion, PLLC

(57) ABSTRACT

An oxygen enriching apparatus which can supply oxygen or oxygen-enriched gas to a user at proper timings, as well as a controller and recording medium therefore. In step 100, a signal from a pressure sensor 53 is input. In subsequent step 110, on the basis of the signal output from the pressure sensor 53, a judgment is made as to whether the state of inhalation can be detected. When the result of judgment is "Yes," this means that an anomalous state exists. In this case, the processing proceeds to step 120. When the result of judgment is "No," this means that the patient and the apparatus are normal. In this case, the present processing is suspended. When start of inhalation cannot be detected over, for example, a period of 10 seconds or more, an anomalous state is judged to have arisen. In step 120, because of the anomalous state having arisen, the electromagnetic valve 47 is driven to open the supply passage 29 so as to supply oxygen-enriched gas over a period of about 4 seconds. Subsequently, the present processing is suspended.

17 Claims, 4 Drawing Sheets

U.S. PATENT DOCUMENTS

| | | | |
|---|---|---|---|
| 5,603,315 A * | 2/1997 | Sasso, Jr. | 128/204.18 |
| 5,626,131 A * | 5/1997 | Chua et al. | 128/204.23 |
| 5,697,364 A | 12/1997 | Chua et al. | |
| 5,720,276 A | 2/1998 | Kobatake et al. | 128/204.18 |
| 6,123,074 A | 9/2000 | Hete et al. | |
| 6,237,594 B1 * | 5/2001 | Davenport | 128/204.26 |
| 6,289,890 B1 * | 9/2001 | Bliss et al. | 128/203.11 |
| 6,378,520 B1 | 4/2002 | Davenport | |

* cited by examiner

[FIG. 1]
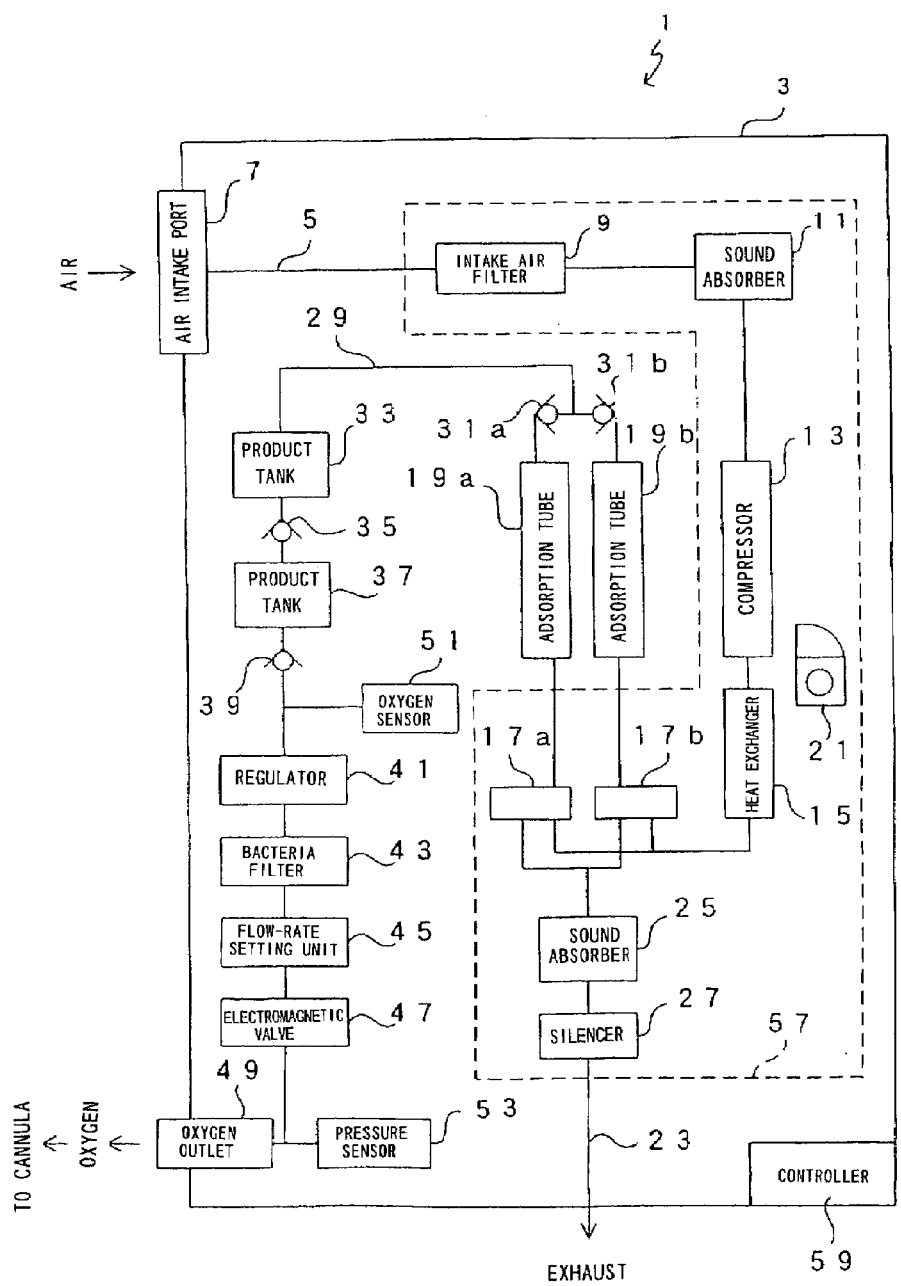

[FIG. 2]
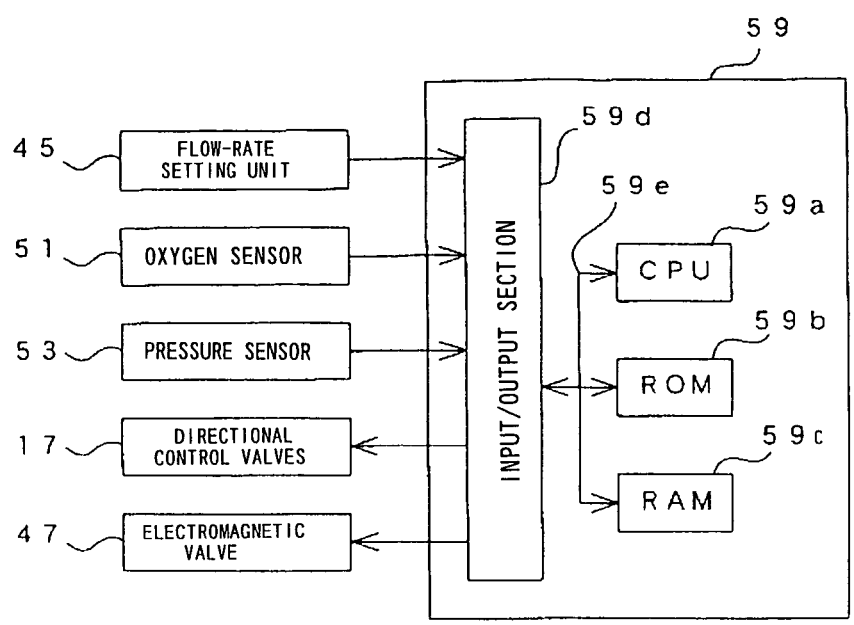

[FIG. 3]
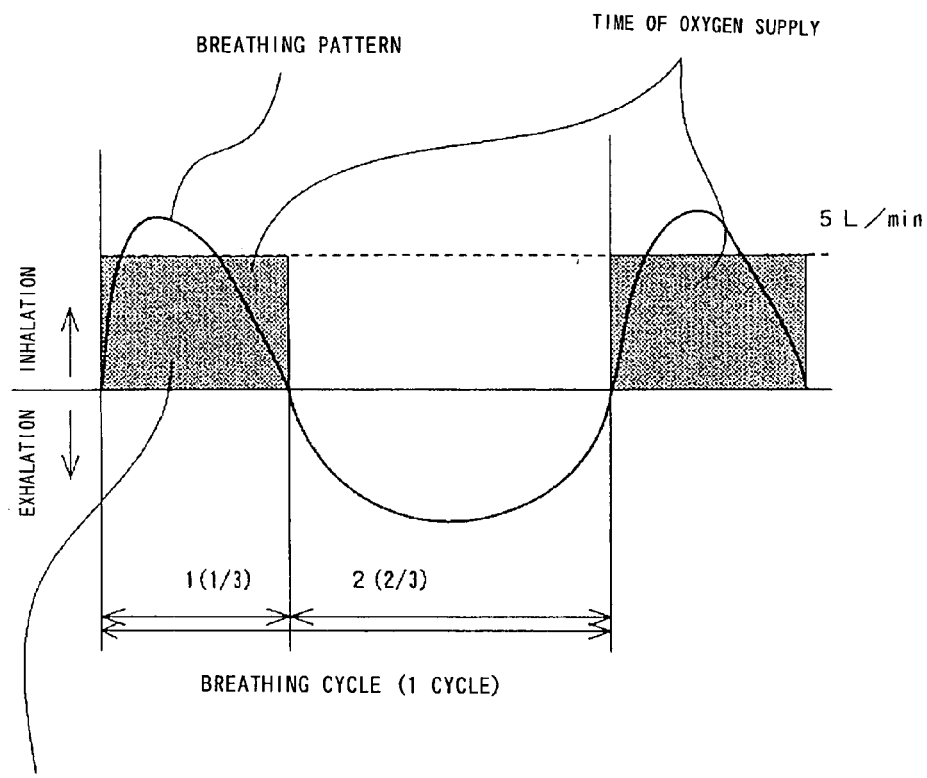

[FIG. 4]
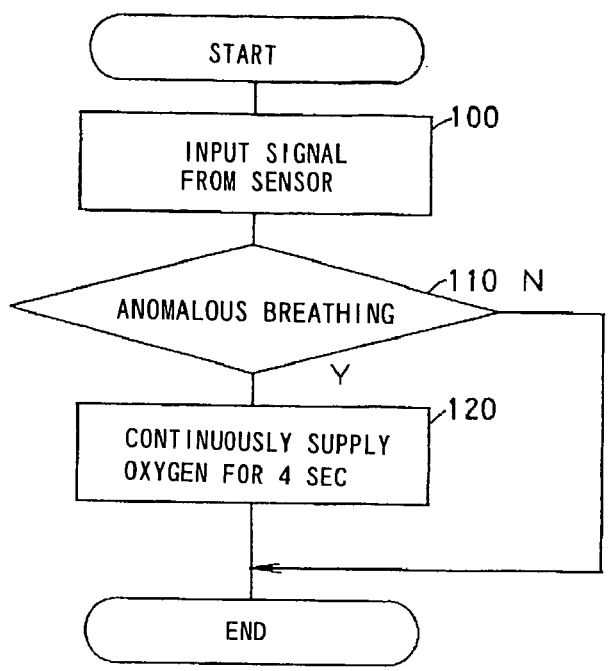

OXYGEN SUPPLY APPARATUS, CONTROLLER FOR THE OXYGEN SUPPLY APPARATUS, AND RECORDING MEDIUM FOR THE CONTROLLER

BACKGROUND OF THE INVENTION

1. Field of the Invention

The present invention relates to an oxygen supply apparatus capable of supplying oxygen or oxygen-enriched gas to, for example, a patient, synchronously with breathing of the patient. The present invention further relates to a controller for the oxygen supply apparatus and to a recording medium for the controller.

2. Description of the Related Art

Examples of conventional known apparatuses for supplying high-concentration oxygen to a patient include an oxygen cylinder filled with oxygen gas, and an oxygen enriching apparatus for medical use capable of producing oxygen-enriched gas from, for example, air through adsorption removal of nitrogen contained in the air and supplying the gas to a patient.

Of these, the oxygen enriching apparatus is used by, for example, a patient who recuperates his/her health over a long time at home, because the oxygen enriching apparatus can supply oxygen-enriched gas over a long time. Since a patient who uses such an oxygen enriching apparatus is weak in lung function as compared with healthy persons, the patient must use the oxygen enriching apparatus all day long. Thereforee, an oxygen enriching apparatus which can be used conveniently for daily living has been in demand.

Meanwhile, since the oxygen cylinder is small in size and is easy to carry about, the oxygen cylinder is used as a portable apparatus which a patient carries with him or her during travel or at the time of visiting a hospital.

Since such an oxygen cylinder has a limited supply of oxygen, a breath synchronizer for supplying oxygen synchronously with breathing is used so as to reduce consumption of oxygen supplied from the cylinder, to thereby extend the service life of the oxygen cylinder.

The breath synchronizer utilizes the rule of thumb that in the case of a human the ratio between the inhalation period and the exhalation period is 1:2. Upon detection of inhalation by means of a sensor, the breath synchronizer supplies high-concentration oxygen from the oxygen cylinder over a short period of time (in the manner of a pulse).

In recent years, a technique has been proposed for applying to an oxygen enriching apparatus the breath synchronization technique used with an oxygen cylinder (see, for example, Japanese Patent Application Laid-Open (kokai) No. 8-187289).

3. Problems to be Solved by the Invention

When oxygen is supplied by means of the above-described breath-synchronized operation, a timing of start of inhalation is detected by use of, for example, a pressure sensor, and oxygen is supplied during the inhalation period. However, in some cases, the timing of start of inhalation cannot be detected due to a certain cause.

Therefore, a situation may occur in which oxygen cannot be supplied at proper timings, and a measure for such a situation is required.

SUMMARY OF THE INVENTION

The present invention has been achieved to solve the above-described problems of the prior art. It is therefore an object of the present invention to provide an oxygen enriching apparatus which can supply oxygen or oxygen-enriched gas to a user at proper timings, as well as a controller and recording medium therefore.

The above objectives have been achieved in a first embodiment of the invention, by providing:

(1) An oxygen supply apparatus which supplies oxygen or oxygen-enriched gas to a user having a breathing cycle including an inhalation period and an exhalation period synchronously with breathing of the user by means of a breath synchronization function, which comprises a sensor for detecting the state of breathing of the user, means for judging the state of breathing of the user under a predetermined judgment condition when breath-synchronized operation is performed, based on a signal from the sensor (corresponding structure for performing the claimed function: controller (59)); and means for supplying the oxygen or oxygen-enriched gas to the user over a predetermined period when the state of breathing of the user cannot be accurately determined (corresponding structure for performing the claimed function: combination of controller (59) and electromagnetic valve (47)).

In the present invention, when breath-synchronized operation is performed, based on a signal from the sensor, the oxygen supply apparatus judges the state of breathing of the user under a predetermined judgment condition. When it is judged that the state of breathing of the user cannot be accurately determined (e.g., when the sensor detects no inhalation over a predetermined judgment period), the oxygen supply apparatus supplies the oxygen or oxygen-enriched gas to the user over a predetermined period.

Therefore, even when the sensor or the like functions irregularly, oxygen or oxygen-enriched gas can be supplied to the patient quickly. Therefore, safety is considerably high.

(2) A second embodiment of the invention comprises an oxygen cylinder filled with oxygen, or an oxygen enriching apparatus which enriches oxygen contained in air.

Here, examples of the oxygen supply apparatus are shown. The control described in the first embodiment can be applied to the case in which oxygen is supplied from an oxygen cylinder or the case in which oxygen-enriched gas is supplied from an oxygen enriching apparatus.

Examples of the oxygen enriching apparatus include an oxygen enriching apparatus which uses an adsorbent for selectively adsorbing and removing nitrogen contained in air, and an oxygen enriching apparatus which uses a membrane that is permeable to oxygen.

(3) In a third embodiment of the invention, the predetermined judgment condition is such that a period during which the state of breathing of the user cannot be accurately determined is a period corresponding to a breathing rate (i.e., the number of times of breath synchronization) of 7 times/min or less.

The breathing rate of 7 times/min is considerably slow, and in that case, the length of each breathing cycle is about 8.57 seconds (60 seconds/7 times). When no breathing can be detected over a period corresponding to a breathing rate slower than the above breathing rate; i.e., over a period over about 8.57 seconds, the state of breathing (or the apparatus) is judged to have become anomalous.

By virtue of the above feature, judgment of an anomaly can be performed accurately, while providing a margin for safety.

(4) In a fourth embodiment of the invention, the predetermined judgment condition is such that a period during which the state of breathing of the user cannot be accurately determined is 8 seconds or more.

When no breathing can be detected over that period, the state of breathing (or the apparatus) is judged to have become anomalous.

By virtue of the above feature, judgment of an anomaly can be performed accurately, while providing a margin for safety.

(5) In a fifth embodiment of the invention, the predetermined period is a time corresponding to 25 to 40% the length of each breathing cycle at a time when the breathing rate is 5 to 7 times/min.

The length of each inhalation period becomes longest when the breathing rate becomes the slowest. In the present embodiment, in consideration of safety, a long inhalation period (corresponding to a slow breathing rate of 5 to 7 times/min) is set, and oxygen or oxygen-enriched gas is supplied over the long inhalation period (e.g., 4 seconds). Therefore, even when breath synchronization by use of the sensor is not attained, or breathing of the patient stops temporarily, a high degree of safety can be secured.

Specifically, the length of a breathing cycle in the case of the breathing rate being 5 to 7 times/min is 12 seconds (60 seconds/5 times) to about 8.57 seconds (60 seconds/7 times); and 25 to 40% the length is 4.8 seconds (12 seconds× 0.4) to 2.15 seconds (about 8.57 seconds×0.25).

Within the above range, 4 seconds is employed as the predetermined period, for the following reason.

Although in the case of a human the breathing rate (per min) is typically 20 times on average, the breathing rate is expected to vary within a range of 5 to 50 times. In the slowest case (5 times), the length of each breathing cycle is 12 seconds. Further, in general, in each breathing cycle, the inhalation period accounts for ⅓, and the exhalation period accounts for ⅔. Therefore, in the slowest case (5 times), 4 seconds (⅓ of 12 seconds) corresponds to the inhalation period.

(6) In a sixth embodiment of the invention, the sensor is a sensor disposed at an oxygen outlet to which oxygen or oxygen-enriched gas is supplied and is adapted to detect the state of a gas at that position.

The present embodiment exemplifies the position of the sensor.

For example, when breath-synchronized operation is performed such that oxygen is supplied during each inhalation period and the supply of the oxygen-enriched gas is stopped during each exhalation period, the user's breathing state (e.g., timing of start of inhalation) can be detected accurately by use of a sensor disposed at the oxygen outlet.

(7) In a seventh embodiment of the invention, the sensor is a sensor disposed at a breath detection port (to which neither oxygen nor oxygen-enriched gas is supplied) provided separately from an oxygen outlet to which oxygen or oxygen-enriched gas is supplied, and is adapted to detect the state of a gas at that position.

The present embodiment exemplifies the position of the sensor.

For example, when breath-synchronized operation is performed such that oxygen is supplied at high flow rate during each inhalation period and at a low flow rate during each exhalation period, in some cases, the user's breathing state cannot be detected accurately by use of the sensor disposed at the oxygen outlet.

By contrast, in the present embodiment, since the sensor is disposed at the breath detection port (to which neither oxygen nor oxygen-enriched gas is supplied), the user's breathing state (e.g., timing of start of inhalation) can be detected accurately even when the breath-synchronized operation is performed such that oxygen is supplied continuously (however, the supply flow rate varies).

(8) In an eighth embodiment of the invention, the sensor is a pressure sensor, a strain gauge sensor, or a piezoelectric sensor.

The present embodiment exemplifies the sensor. Use of the pressure sensor enables detection of variation in the air pressure within, for example, a cannula, which varies in accordance with breathing of the user. Use of the strain gauge sensor enables detection, as strain variation, of deformation of a diaphragm which moves in accordance with breathing of the user. Use of the piezoelectric sensor enables detection of vibration or sound which is generated in accordance with breathing of the user.

Examples of the pressure sensor include a diaphragm-type pressure sensor and a sensor which detects pressure or differential pressure from variation in electrostatic capacitance.

(9) In a ninth embodiment of the invention, the oxygen supply apparatus is an oxygen enriching apparatus. When the breath-synchronized operation is not performed, the oxygen enriching apparatus supplies the oxygen-enriched gas at a flow rate (first flow rate) equal to or less than a continuous base flow rate, which represents a flow rate at which the oxygen enriching apparatus can supply the oxygen-enriched gas continuously (that is, a continuous supply capacity which represents the maximum flow rate at which the oxygen enriching apparatus can supply oxygen-enriched gas continuously; e.g., 2 liters/min). When the breath-synchronized operation is performed, the oxygen enriching apparatus supplies the oxygen-enriched gas during the inhalation period of a breathing cycle at a flow rate (second flow rate; e.g., 5 liters/min) greater than the continuous base flow rate and stops supply of the oxygen-enriched gas during the exhalation period of the breathing cycle.

The present embodiment exemplifies the control of the oxygen enriching apparatus.

In the case of a 2 liter model, when breath-synchronized operation is not performed, oxygen-enriched gas can be supplied continuously at 2 liters/min (maximum). When the breath-synchronized operation is performed with designation of a flow rate greater than the continuous flow rate, the oxygen-enriched gas is supplied at a high flow rate of, for example, 5 liters/min during each inhalation period, and the supply of the oxygen-enriched gas is stopped during each exhalation period.

Therefore, even when a small apparatus such as a 2 liter model is used, oxygen-enriched gas can be supplied at a high flow rate of, for example, 5 liters/min when necessary.

Accordingly, the apparatus can be made compact, and the following effects can be achieved, among others. (1) Since the volume and weight of the oxygen enriching apparatus do not increase, the burden imposed on a sales representative or a caregiver can be decreased. (2) Since electrical-power consumption does not increase, electricity cost is low. (3) Since the level of noise is low, the noise does not hinder good sleep of the patient. In addition, even when a measure against the noise is employed, the volume and weight of the oxygen enriching apparatus do not increase very much.

(10) In a tenth embodiment of the invention, the oxygen supply apparatus is an oxygen enriching apparatus. When the breath-synchronized operation is performed, the oxygen enriching apparatus supplies the oxygen-enriched gas during the inhalation period of a breathing cycle at a flow rate (third flow rate; e.g., 5 liters/min) greater than the continuous base flow rate (e.g., 3 liters/min), which represents a flow rate at which the oxygen enriching apparatus can supply the oxygen-enriched gas continuously, and supplies the oxygen-enriched gas during the exhalation period of the breathing cycle at a flow rate (fourth flow rate; e.g., 2 liters/min) less than the continuous base flow rate.

The present embodiment exemplifies the control of the oxygen enriching apparatus.

When a flow rate greater than the continuous base flow rate is designated, oxygen-enriched gas is supplied at a high flow rate of, for example, 5 liters/min over each inhalation period, and at a low flow rate of, for example, 2 liters/min over each exhalation period.

Therefore, even when a small apparatus such as a 3 liter model is used, oxygen-enriched gas can be supplied at a high flow rate of, for example, 5 liters/min when necessary.

Accordingly, the apparatus can be made compact, and the following effects can be achieved, among others. (1) Since the volume and weight of the oxygen enriching apparatus do not increase, the burden imposed on a sales representative or a caregiver can be decreased. (2) Since electrical power consumption does not increase, electricity cost is low. (3) Since the level of noise is low, the noise does not hinder good sleep of the patient. In addition, even when a measure against the noise is employed, the volume and weight of the oxygen enriching apparatus do not increase very much.

(11) In an eleventh embodiment of the invention, when the breath-synchronized operation is not performed, the oxygen enriching apparatus supplies the oxygen-enriched gas at a flow rate (fifth flow rate) equal to or less than the continuous base flow rate, which represents a flow rate at which the oxygen enriching apparatus can supply the oxygen-enriched gas continuously.

The present embodiment exemplifies the control according to the ninth embodiment that is performed when the breath-synchronized operation is not carried out.

Notably, each of the above-described continuous base flow rate, first flow rate, second flow rate, third flow rate, fourth flow rate, and fifth flow rate is a unit flow rate which represents an amount of oxygen-enriched gas supplied over a certain time and can be represented by a volume of a gas (at 1 atm) supplied over, for example, 1 min.

(12) In a twelfth embodiment of the invention, the continuous base flow rate is 4 liters/min or less.

Since the apparatus can be made compact, the effects (1) to (3) described in relation to the eighth embodiment can be achieved.

(13) A thirteenth embodiment of the invention is directed to a controller for controlling operation of the oxygen enriching apparatus.

The controller may be integrated with (built in) the oxygen enriching apparatus or may be separated from the oxygen enriching apparatus.

(14) A fourteenth embodiment of the invention is directed to a recording medium having recorded thereon means (e.g., a program) for executing the function of the controller.

When the function of the controller is realized by use of a computer system, the function can be provided in the form of a program which is executed in the computer system. Such a program can be recorded on a computer-readable medium, such as a floppy disk, a magnetic optical disk, CD-ROM, or a hard disk drive, and when necessary can be loaded on the computer system and started so as to use the program. Alternatively, the program may be stored in ROM or backup RAM serving as a computer-readable recording medium, which is then incorporated into the computer system.

BRIEF DESCRIPTION OF THE DRAWINGS

FIG. 1 is an explanatory view showing the basic structure of an oxygen enriching apparatus of an embodiment of the invention.

FIG. 2 is a block diagram showing the electrical configuration of a controller of the oxygen enriching apparatus of the embodiment.

FIG. 3 is an explanatory view showing breathing cycles.

FIG. 4 is a flowchart showing the control processing performed by the controller of the embodiment.

DESCRIPTION OF REFERENCE NUMERALS

1: oxygen enriching apparatus
19a, 19b, 19: adsorption tubes
17a, 17b, 17: directional control valves
33, 37: product tanks
31a, 31b, 35, 39: check valves
45: flow-rate setting unit
44: electromagnetic valve
53: pressure sensor
59: controller

DETAILED DESCRIPTION OF THE PREFERRED EMBODIMENTS

An example mode (embodiment) of the oxygen supply apparatus, controller, and recording medium of the present invention will be described with reference to the drawings. However, the present invention should not be construed as being limited thereto.

The embodiment will be described, taking an oxygen enriching apparatus for medical use (hereinafter referred to as an "oxygen enriching apparatus") which has a built-in controller as an example of the oxygen supply apparatus.

The oxygen enriching apparatus of the present embodiment enriches oxygen contained in air through adsorption removal of nitrogen from the air and continuously supplies an oxygen-enriched gas to a patient, which is a user, at a first flow rate (e.g., 2 liters/min), which is equal to or less than a continuous base flow rate. Further, in case of need, the oxygen enriching apparatus switches its operation to breath-synchronized operation in order to supply the oxygen-enriched gas over each inhalation period only of the patient at a second flow rate (e.g., 5 liters/min), which is greater than the continuous base flow rate.

a) First, the basic structure of the oxygen enriching apparatus will be described.

As shown in FIG. 1, the oxygen enriching apparatus 1 of the present embodiment is accommodated in a main-body case 3. In an air introduction passage 5 are provided, in the sequence given from the upstream end, an air intake port 7, an intake air filter 9 for removing dust and dirt, a sound absorber 11 for lowering sound generated upon intake of air, a compressor 13 for compressing air, a heat exchanger 15 for cooling compressed air, a pair of directional control valves 17a and 17b (collectively denoted by 17) for switching between three flow passages, and a pair of adsorption tubes 19a and 19b (collectively denoted by 19).

A sirocco fan 21 for cooling the compressor 13 and the heat exchanger 15 is provided in the vicinity thereof.

A sound absorber 25 similar to the above and a silencer 27 for eliminating intermittent exhaust noise are provided in a discharge passage 23, which extends from the directional control valves 17 and is adapted to discharge nitrogen from the pair of adsorption tubes 19.

Moreover, in a supply passage 29, which extends from the pair of adsorption tubes 19 and is adapted to supply oxygen-enriched gas, are provided, in the sequence given from the upstream side, a pair of check valves 31a and 31b for preventing reverse flow toward the adsorption tubes 19, a first product tank 33 for storing oxygen-enriched gas, a check valve 35 for preventing reverse flow toward the first product tank 33, a second product tank 37 for storing oxygen-enriched gas, a check valve 39 for preventing reverse flow toward the second product tank 37, a regulator 41 for lowering the pressure of oxygen, a bacteria filter 43 for preventing passage of bacteria or the like, a flow-rate setting unit 45 for setting a supply flow rate of oxygen-enriched gas, an electromagnetic valve 47 for opening/closing a flow passage, and an oxygen outlet 49 for supplying oxygen-enriched gas.

An oxygen sensor 51 for detecting oxygen concentration is disposed between the check valve 39 and the regulator 41; and a pressure sensor 53 for detecting pressure at the time of inhalation is disposed between the electromagnetic valve 47 and the oxygen outlet 49.

Moreover, as shown by a broken line in FIG. 1, in the oxygen enriching apparatus 1 of the present embodiment, not only the compressor 13 but also the intake air filter 9, the sound absorbers 11 and 25, the heat exchanger 15, the directional control valves 17, the silencer 27, and the sirocco fan 21 are accommodated within a metal case 57 lined with vibration-absorbing rubber and a sound-absorbing material to thereby reduce noise during operation.

The oxygen enriching apparatus 1 having the above-described structure is a small apparatus whose continuous base flow rate is 2 liters/min. The apparatus has a weight of 30 kg, a power consumption of 170 W, and operating noise of 30 dB or less.

b) Next, the above-described respective components will be described in more detail.

Each of the above-described directional control valves 17 is a three-port directional control valve which operates under control of a controller 59. Through changeover operation, the directional control valves 17 selectively create a state in which the communication between the heat exchanger 15 and the adsorption tubes 19 is established and the communication between the adsorption tubes 19 and the discharge passage 23 is broken, and a state in which the communication between the heat exchanger 15 and the adsorption tubes 19 is broken and the communication between the adsorption tubes 19 and the discharge passage 23 is established.

The pair of adsorption tubes 19 are filled with a zeolite-containing adsorbent. This adsorbent has characteristics such that when pressurized (to, e.g., 2 atm (gauge pressure)), the adsorbent preferentially adsorbs nitrogen contained in air; and when the pressure is lowered (to, e.g., atmospheric pressure), the adsorbent releases the adsorbed nitrogen in order to self-regenerate.

The product tanks 33 and 37 each have a capacity of 750 ml and form a reservoir for oxygen-enriched gas.

That is, the product tanks 33 and 37 suppress variations in supply amount of oxygen-enriched gas to thereby enable continuous supply. Further, even when oxygen-enriched gas is supplied intermittently at a high flow rate, the product tanks 33 and 37 secure a sufficient supply capacity and prevent pressure fluctuations due to start and stop of supply of oxygen-enriched gas from propagating to the adsorption tubes 19.

The check valve 35 disposed between the product tanks 33 and 37, in cooperation with the function of the product tanks 33 and 37, prevents propagation of pressure fluctuations to the adsorption tubes 19, which propagation would otherwise occur due to intermittent supply of oxygen-enriched gas.

The regulator 41 reduces the pressure of oxygen-enriched gas from 2 atm, at which oxygen-enriched gas is supplied from the production tanks 33 and 37, to 0.35 atm (gauge pressure), at which a patient inhales the gas with ease.

The flow-rate setting unit 45 enables manual flow-rate setting.

That is, by adjusting an orifice, the continuous flow rate (first flow rate) can be set within a range up to the continuous base flow rate (2 liters/min). When a flow rate greater than the continuous base flow rate is set, oxygen-enriched gas cannot be supplied continuously. Therefore, the control is switched to breath-synchronized control in order to enable supply of oxygen-enriched gas at the set flow rate (second flow rate).

Specifically, the orifice is adjusted in accordance with the set flow rate (the orifice is set to an opening that enables supply at 5 liters/min (maximum)), and breath-synchronized control is started.

A tube extending from an unillustrated cannula (nasal cannula) used by a patient is connected to the oxygen outlet 49. Accordingly, oxygen-enriched gas is supplied from the oxygen outlet 49 at a predetermined flow rate (the first or second flow rate) set by use of the flow-rate setting unit 45 and under pressure reduced to 0.35 atm by means of the regulator 41.

c) Next, the electrical configuration of the controller 59 and other components for controlling the oxygen enriching apparatus 1 will be described.

In the present embodiment, as shown in FIG. 2, the controller 59 includes a microcomputer as a main element and is disposed inside the oxygen enriching apparatus 1. The controller 59 includes a CPU 59a, ROM 59b, RAM 59c, an input/output section 59d, a bus line 59e, etc., which are well known.

The flow-rate setting unit 45, the oxygen sensor 51, and the pressure sensor 53 are connected to the input/output section 59d of the controller 59. Further, the directional control valves 17 and the electromagnetic valve 47 are connected to the input/output section 59d as actuators.

Thus, the controller 59 performs a predetermined calculation on the basis of signals obtained from the flow-rate setting unit 45, the oxygen sensor 51, and the pressure sensor 53, and controls the operations of the directional control valves 17 and the electromagnetic valve 47.

d) Next, a breath synchronization function, which is a major function of the oxygen enriching apparatus 1 according to the present embodiment, will be described.

The highly-sensitive pressure sensor (e.g., a semiconductor pressure sensor) 55 connected to the vicinity of the oxygen outlet 49 detects a slight negative pressure (0.4 mmH2O) which is produced when the patient inhales oxygen via the cannula. In response to detection of the negative pressure, the controller 59 opens and closes the electromagnetic valve 47 such that oxygen-enriched gas is supplied over the inhalation period of each breathing cycle of the patient, as shown in FIG. 3.

In the case of a human, in general, each inhalation period accounts for ⅓ of a corresponding breathing cycle, and each exhalation period accounts for ⅔ of a corresponding breathing cycle. Therefore, oxygen-enriched gas is supplied over the inhalation period only at the high flow rate, which is higher than the continuous base flow rate.

Through the above-described operation, oxygen-enriched gas is supplied to the patient only when the patient inhales oxygen, and the supply of oxygen-enriched gas is stopped during each exhalation period. Thus, during each exhalation period, oxygen-enriched gas can be stored in the product tanks 33 and 37.

Moreover, in the present embodiment, the controller 59 detects inhalation by use of the pressure sensor 53; calculates an averaged breathing cycle time from an average value of the past two to five breathing cycle times; regards one-third of the averaged breathing cycle time as an inhalation period; and opens the electromagnetic valve 47 over the inhalation period to thereby supply oxygen-enriched gas to the patient.

e) Next, control for occurrence of an anomalous state, which is the main portion of the control processing performed in the controller 59, will be described with reference to the flowchart of FIG. 4.

First, in step 100 of FIG. 4, the controller 59 inputs a signal output from the pressure sensor 53.

In subsequent step 110, on the basis of the signal output from the pressure sensor 53, the controller 59 judges whether the state of inhalation can be detected. When the result of judgment is "Yes," this means that an anomalous state exists. In this case, the controller 59 proceeds to step 120. When the result of judgment is "No," this means that the patient and the apparatus are normal. In this case, the controller 59 suspends the present processing.

When start of inhalation cannot be detected over, for example, 10 seconds or more, the controller 59 judges that the patient or a device such as the pressure sensor 53 has come into an anomalous state.

In step 120, because of the anomalous state having arisen, the controller 59 drives the electromagnetic valve 47 to open the supply passage 29 so as to supply oxygen-enriched gas over about 4 seconds. Subsequently, the controller 59 suspends the present processing.

f) As described above, the oxygen enriching apparatus 1 of the present embodiment detects the state of inhalation by use of the pressure sensor 53, and when start of breathing cannot be detected over, for example, 10 seconds or more, the controller 59 supplies oxygen-enriched gas over about 4 seconds at a predetermined flow rate (e.g., 5 liters/min).

Accordingly, when there is a possibility of the breathing of the patient having come into an anomalous state, oxygen-enriched gas can be supplied quickly at a sufficient flow rate. Therefore, safety is considerably high.

Moreover, although the oxygen enriching apparatus 1 of the present embodiment is a small apparatus capable of supplying oxygen-enriched gas continuously, when a flow rate greater than the continuous base flow rate is set by use of the flow-rate adjuster 45, the oxygen enriching apparatus 1 automatically starts breath-synchronized control in order to supply oxygen-enriched gas to the patient over each inhalation period at a high flow rate of 5 liters/min.

In other words, in spite of the small apparatus size, the oxygen enriching apparatus 1 can supply oxygen at a high flow rate over each inhalation period.

Accordingly, the oxygen enriching apparatus 1 of the present embodiment achieves the following effects, among others. (1) Since the volume and weight of the oxygen enriching apparatus do not increase, the burden imposed on a sales representative or a caregiver can be decreased. (2) Since electrical-power consumption does not increase, electricity cost is low. (3) Since the level of noise is low, the noise does not hinder good sleep of the patient. In addition, even when a measure against noise is employed, the volume and weight of the oxygen enriching apparatus do not increase very much.

The present invention is not limited to the above-described embodiment, and may be practiced in various forms without departing from the scope of the present invention. For example:

(1) In the above-described embodiment, an oxygen enriching apparatus and a controller therefore have been described. However, the present invention is not limited thereto, and encompasses a recording medium which stores means for executing the above-described processing.

Examples of such a recording medium include a microchip, a floppy disk, a hard disk drive, an optical disk, and electronic control devices (ROM, RAM, EPROM, etc.) which are incorporated in a microcomputer. In other words, no limitation is imposed on the recording medium, insofar as the selected recording medium stores means, such as a program, which can execute the above-described processing of the oxygen enriching apparatus and the controller.

(2) The above-described embodiment exemplifies the case in which the controller is built in the oxygen enriching apparatus. However, the controller may be separated from the oxygen enriching apparatus. In this case, a user can operate the controller at hand, which is convenient for the user.

(3) The above-described embodiment exemplifies the case in which breath-synchronized operation is performed such that supply of oxygen-enriched gas is stopped during each exhalation period. However, the breath-synchronized operation may be performed in such manner that oxygen-enriched gas is supplied at a high flow rate during each inhalation period and at a low flow rate during each exhalation period.

In this case, since oxygen-enriched gas is supplied over the entire period of each breathing cycle, the unnatural sensation that a patient feels can be made very mild.

(4) The above-described embodiment exemplifies the case in which a cannula is connected to the oxygen outlet. However, in addition to the oxygen outlet, a breath detection port (to which no oxygen-enriched gas is supplied) may be provided, and a pressure sensor may be disposed at the breath detection port.

This technique has an advantage such that the state of breathing can be detected accurately when breath-synchronized operation is performed to supply oxygen-enriched gas in both inhalation and exhalation periods.

(5) The above-described embodiment exemplifies an oxygen enriching apparatus. However, the control performed at the time of occurrence of the anomalous state can be applied to the case in which oxygen is supplied from an oxygen cylinder.

EFFECTS OF THE INVENTION

In the present invention, the state of breathing is detected using a sensor; and when the state of breathing has been judged to be anomalous, oxygen or oxygen-enriched gas is supplied over a predetermined period. Therefore, safety is very high.

This application is based on Japanese Patent Application No. 2000-287110 filed Sep. 21, 2000 the disclosure of which is incorporated herein by reference in its entirety.

What is claimed is:

1. An oxygen supply apparatus which supplies oxygen or oxygen-enriched gas to a user having a breathing cycle including an inhalation period and an exhalation period synchronously with breathing of the user by means of a breath synchronization function, which comprises:

a sensor for detecting the state of breathing of the user;

means for judging the state of breathing of the user under a predetermined judgment condition when breath-synchronized operation is performed, based on a signal from the sensor; and means for supplying the oxygen or oxygen-enriched gas to the user over a predetermined period of from 2.15 to 4.8 seconds when no breathing is detected.

2. The oxygen supply apparatus as claimed in claim 1, which comprises an oxygen cylinder filled with oxygen, or an oxygen enriching apparatus which enriches oxygen contained in air.

3. The oxygen supply apparatus as claimed in claim 2, wherein the predetermined judgment condition is such that a period during which the state of breathing of the user cannot be detected is a period corresponding to a breathing rate of 7 times/mm or less.

4. The oxygen supply apparatus as claimed in claim 3, wherein the predetermined judgment condition is such that a period during which the state of breathing of the user cannot be detected is 8 seconds or longer.

5. The oxygen supply apparatus as claimed in claim 1, wherein the predetermined period is a time corresponding to 25 to 40% the length of each breathing cycle at a time when the breathing rate is 5 to 7 times/mm.

6. The oxygen supply apparatus as claimed in claim 1, wherein the sensor is disposed at an oxygen outlet to which oxygen or oxygen-enriched gas is supplied and is adapted to detect the state of a gas at that position.

7. The oxygen supply apparatus as claimed in claim 1, wherein the sensor is disposed at a breath detection port provided separately from an oxygen outlet to which oxygen or oxygen-enriched gas is supplied, and is adapted to detect the state of a gas at that position.

8. The oxygen supply apparatus as claimed in claim 1, wherein the sensor is a pressure sensor, a strain gauge sensor, or a piezoelectric sensor.

9. The oxygen supply apparatus as claimed in claim 1, wherein the oxygen supply apparatus is an oxygen enriching apparatus;

when the breath-synchronized operation is not performed, the oxygen enriching apparatus supplies the oxygen-enriched gas at a flow rate equal to or less than a continuous base flow rate that is the flow rate at which the oxygen enriching apparatus can supply the oxygen-enriched gas continuously; and when the breath-synchronized operation is performed, the oxygen enriching apparatus supplies the oxygen-enriched gas during the inhalation period of a breathing cycle at a flow rate greater than the continuous base flow rate and stops supply of the oxygen-enriched gas during the exhalation period of the breathing cycle.

10. The oxygen supply apparatus as claimed in claim 1, wherein the oxygen supply apparatus is an oxygen enriching apparatus; and when the breath-synchronized operation is performed, the oxygen enriching apparatus supplies the oxygen-enriched gas during the inhalation period of a breathing cycle at a flow rate greater than a continuous base flow rate that is the flow rate at which the oxygen enriching apparatus can supply the oxygen-enriched gas continuously, and supplies the oxygen-enriched gas during the exhalation period of a breathing cycle at a flow rate less than the continuous base flow rate.

11. The oxygen supply apparatus as claimed in claim 10, wherein when the breath-synchronized operation is not performed, the oxygen enriching apparatus supplies the oxygen-enriched gas at a flow rate equal to or less than a continuous base flow rate that is the flow rate at which the oxygen enriching apparatus can supply the oxygen-enriched gas continuously.

12. The oxygen supply apparatus as claimed in claim 9, wherein the continuous base flow rate is 4 liters/mm or less.

13. The oxygen supply apparatus as claimed in claim 10, wherein the continuous base flow rate is 4 liters/mm or less.

14. The oxygen supply apparatus as claimed in claim 11, wherein the continuous base flow rate is 4 liters/mm or less.

15. A controller for controlling operation of an oxygen supply apparatus which supplies oxygen or oxygen-enriched gas to a user having a breathing cycle including an inhalation period and an exhalation period synchronously with breathing of the user by means of a breath synchronization function, which comprises:

a sensor for detecting the state of breathing of the user;

means for judging the state of breathing of the user under a predetermined judgment condition when breath-synchronized operation is performed, based on a signal from the sensor; and means for supplying the oxygen or oxygen-enriched gas to the user over a predetermined period of from 2.15 to 4.8 seconds when no breathing is detected.

16. A recording medium having recorded thereon means for executing the function of a controller for controlling operation of an oxygen supply apparatus which supplies oxygen or oxygen-enriched gas to a user having a breathing cycle including an inhalation period and an exhalation period synchronously with breathing of the user by means of a breath synchronization function, which comprises:

a sensor for detecting the state of breathing of the user;

means for judging the state of breathing of the user under a predetermined judgment condition when breath-synchronized operation is performed based on a signal from the sensor; and means for supplying the oxygen or oxygen-enriched gas to the user over a predetermined period of from 2.15 to 4.8 seconds when no breathing is detected.

17. The oxygen supply apparatus as claimed in claim 1, wherein oxygen or oxygen-enriched gas is supplied to the user over a period of about four seconds when no breathing is detected.

* * * * *